United States Patent
Tiwet et al.

(10) Patent No.: US 7,504,959 B2
(45) Date of Patent: Mar. 17, 2009

(54) GAS MONITORING USING ELECTROCHEMICAL CELL AND METHOD OF OPERATING

(75) Inventors: John A. Tiwet, Waukegan, IL (US); Cary S. Stone, Prospect Heights, IL (US); Richard A. Gorny, Des Plaines, IL (US); John Chapples, Drayton (GB); Ian Robins, Dorchester (GB)

(73) Assignee: Honeywell Analytics AG, Poole Dorset (GB)

( * ) Notice: Subject to any disclaimer, the term of this patent is extended or adjusted under 35 U.S.C. 154(b) by 41 days.

(21) Appl. No.: 11/737,913

(22) Filed: Apr. 20, 2007

(65) Prior Publication Data

US 2007/0241917 A1  Oct. 18, 2007

Related U.S. Application Data

(63) Continuation of application No. 11/029,145, filed on Jan. 4, 2005, now Pat. No. 7,224,285.

(60) Provisional application No. 60/537,087, filed on Jan. 15, 2004, provisional application No. 60/567,140, filed on Apr. 30, 2004.

(51) Int. Cl.
*G08B 17/10* (2006.01)

(52) U.S. Cl. ............... 340/632; 340/633; 600/500; 600/549; 600/558; 128/205.11; 128/205.24

(58) Field of Classification Search ......... 340/632, 340/633; 600/500, 549, 558; 128/205.11, 128/205.24
See application file for complete search history.

(56) References Cited

U.S. PATENT DOCUMENTS

| 4,526,188 | A | * | 7/1985 | Olsson et al. ........... 137/3 |
| 4,576,159 | A | * | 3/1986 | Hahn et al. ........ 128/203.14 |
| 5,205,322 | A | * | 4/1993 | Merick et al. .......... 137/597 |
| 5,722,449 | A | | 3/1998 | Heinonen et al. |
| 6,076,523 | A | | 6/2000 | Jones et al. |
| 2002/0178783 | A1 | | 12/2002 | Miller et al. |

OTHER PUBLICATIONS

International Search Report and Written Opinion of the International Searching Authority—Generated in conneciton with International App. No. PCT/US05/14753, 4 pages (Sep. 5, 2006).

* cited by examiner

*Primary Examiner*—Tai T Nguyen
(74) *Attorney, Agent, or Firm*—Husch Blackwell Sanders Welsh & Katz (57) ABSTRACT

A method and apparatus for gas detection uses a sensor such as an electrochemical (EC) cell and includes a feedback control loop to control a pump to establish a first predetermined gas flow rate to the EC cell. The concentration of the gas at the first predetermined flow rate is measured. If the detected concentration exceeds a predetermined Alert value at the first flow rate an Initial Warning without remedial action is generated, and, the system then changes the gas flow rate before an Alarm is indicated. An Alarm is signaled only if the system verifies the first measurement. Preferably the first flow rate is set to optimize the measurement accuracy of the EC cell being used, and the second flow rate is lower than the first. Verification of an Alarm at the first flow rate may be conducted quickly by a quick-reaction process. The controller may periodically cycle the flow rates between the first and second rates for better accuracy and faster verification times.

10 Claims, 5 Drawing Sheets

GAS MONITORING USING ELECTROCHEMICAL CELL AND METHOD OF OPERATING

RELATED APPLICATIONS

This application is a Continuation of and claims the benefit of now U.S. Pat. No. 7,224,285, the filing date of U.S. patent application Ser. No. 11/029,145 filed Jan. 4, 2005, which claims the benefit of the filing date of U.S. Provisional Application Ser. No. 60/537,087 filed Jan. 15, 2004, and claims the benefit of the filing date of U.S. Provisional Application Ser. No. 60/567,140 filed Apr. 30, 2004.

FIELD OF THE INVENTION

The present invention relates to monitors using Electrochemical (EC) cells, for detecting and measuring the concentration of gases, typically toxic or other undesirable gases, or liquids.

BACKGROUND OF THE INVENTION

Electrochemical cells are used to detect the presence and measure the concentration of gases or other fluids. Different cells are known to be responsive to different, specific gases or other fluid/sensor combinations where the response of the sensor is affected by the presence of a diffusion layer within the fluid, as with electrochemical cells. The response characteristic (i.e. voltage or current generated by the cell vs. gas flow rate) of a particular EC cell to a specific gas is also known.

EC cells are widely used in industries where toxic or other undesirable gases are present, such as in the manufacture of semiconductors. In such fields, gas monitoring is continuous and reliable. In the event of detection of a gas at a concentration level above an acceptable or safe level, the monitoring system signals an Alarm and communicates the condition to operating personnel. Typically, this is followed by a shutdown of the line.

It is known that electrochemical cells generate electrical signals which are a function of the concentration of known gases. It is also known for such cells that the output signal of the sensor is a function of flow, as will be described further within. The signal generated by the cell is not necessarily a linear function of gas concentration. In addition, however, electrical chemical cells are known to generate electrical signals (sometimes referred to as background signals or noise) which are not related to flow rate or the concentration of the gas under surveillance. That is, for a given gas concentration, EC cells generally have a signal component which is flow-dependent, and another component which is independent of or not related to flow rate.

An important feature of the present invention is to take account of or compensate for the characteristic of electrochemical cells (or other sensors) having a flow-dependent component and a flow-independent component. The flow-independent component may be sensed as related to gas concentration and thus cause detection error.

The present invention accounts for the possibility of an appreciable flow-independent component in the output signal generated by the EC cell by changing the flow rate after a first concentration sample, and measuring gas concentration at two different but known flow rates, or otherwise using the sensor signal at the second flow rate to confirm that the concentration measurement at the first flow rate is reliable, and not the result of the flow-independent component of the sensor output signal in a manner to be described below.

It will be realized that it could be very expensive to shut down a production line, and it is highly undesirable to do so merely because of an incidental failure of equipment or a non-gas-related event or effect such as the presence of background signal related to the sensor cell only or radio frequency interference ("RFI"), which are known to affect detection systems. Thus, due to the cost involved in checking or interrupting a production line, it is highly desirable to avoid the signaling of false alarms. A fault or background signal may exist in the EC cell itself, or a fault may exist in the monitoring system or be due to radio frequency interference or transient electrical conditions, and not necessarily a measure of the concentration of the gas being monitored.

SUMMARY OF THE INVENTION

The present invention includes a flow meter to measure the concentration of the gas being monitored. The monitor, as is known, may draw gas from a larger area under surveillance, and pass the sample through a passage or conduit. A data processor (which may be a microprocessor) monitors a flow rate measurement signal from the flow meter, and controls a gas pump, which in the illustrated embodiment is a diaphragm pump, to establish a first predetermined flow rate for the gas being sampled. Concentration measurements for a particular known gas or gases are taken periodically at the first flow rate. If concentration levels are within an acceptable range or below a predetermined level (referred to as the Alert level), the concentration reading may be displayed and/or recorded with no further action taken to alert personnel.

The primary purpose of the present invention is to enhance the safety of users and personnel within the area being monitored. The present system accomplishes this objective by issuing a signal, referred to as an Initial Warning, when a detected concentration C1 of the gas being monitored at the first flow rate equals or exceeds the Alert level. At this stage, because of the possible errors mentioned above, it is not known for certain whether the sensed signal is an accurate representative of concentration or, perhaps, due to a system fault or other signal error of the type mentioned. Thus, the present invention seeks to confirm or deny that the sensed signal causing the Initial Warning is in fact caused by an undesired concentration of the gas being monitored or by an error or fault. One immediate benefit provided by the invention is a higher level of operator confidence in the issuance of an Alarm following an Initial Warning.

To confirm or deny the presence of a detected concentration at the Alert level for the gas being monitored, a processor-based controller changes the gas flow rate to a second, predetermined value. Normally, for most gases of interest, and particularly where the sensor has a diffusion-limited response characteristic, the second measurement flow rate F2 is lower than the first flow rate F1, but in all cases the second flow rate is different than the first flow rate, known and predetermined by the system.

In a first embodiment of the invention, the gas concentration is then re-measured at the second flow rate. The gas concentration at the second flow rate, C2, preferably is proportional to, but at least representative of the gas concentration (which is known to be flow dependent for most, if not all, EC cells). If the second concentration measurement, C2, confirms that the first concentration measurement, C1, is indeed a matter requiring attention, a suitable notification (e.g. an Alarm) is generated and communicated immediately to operating personnel. If desired, action may be taken automatically by the system. However, if the concentration detected at the first flow rate is not confirmed at the second flow rate, notification is given of the disparity for further investigation, short of any immediate remedial action or Alarm which might cause system shut down.

As used herein, to clarify matters, an "Initial Warning" refers to an "Alert" condition sensed at a first concentration measurement, and it may be an audible, visual or textual signal, or any combination designed to communicate the sensed Alert condition to operating personnel, but short of system shutdown. "Alarm" is used to refer to the confirmation or verification signal at the second flow rate, which may be any similar signal, but also implies that some affirmative remedial action is taken, either by the system itself or by system operators.

The controller has stored in memory, table information specifying desired flow rates and concentration data for particular EC cells and associated gases. Certain EC cells are known to be more accurate when operating with gases flowing at specific rates as persons skilled in the art know. In operation, the system may detect the presence in the apparatus of certain, specific EC cells, as by mechanical configuration or keying or electrical identification, alerting the controller to set the flow rate for optimum sensing capability for the particular cell and gas being monitored, according to the stored table look-up data. This enables the same monitoring system to work with different EC cells, and is particularly advantageous to manufacturers of gas monitoring systems who then need not customize the monitoring system for individual EC cells or for particular gases.

Although it may, in some instances, be acceptable or desirable to determine the concentration of the detected gas at two different flow rates, it must be realized that what is of concern is the reliable detection and confirmation of an Alarm condition as quickly as possible while avoiding false alarms, but not at the expense of safety.

Thus, the present invention further contemplates using an optional "quick response" verification procedure or sequence which, upon initial detection of an Alert condition at the first flow rate, will confirm or verify that the detected Alert condition is in fact being caused by the presence of the gas and not by sensor error or component failure or some other non-flow-dependent factor such as cell background signal or RFI. The "quick response" verification and Alarm sequence may be completed within seconds, not minutes, of the Initial Warning. For example, if a second concentration measurement is to be completed at a different flow level before an Alarm condition is signaled, it may take up to ninety seconds or more to change conditions, take a reading and make a calculation before remedial action is taken or initiated.

A first quick-reaction verification procedure includes adjusting (preferably lowering) the flow rate of the gas to a second, known flow rate while continuing to measure the signal level of the detecting sensor electronically. It is known that the signal output level of the EC cell is a monotonic (i.e. continuously increasing but not necessarily linear) diffusion-limited function of the flow rate of the gas. Thus, in the first quick-reaction verification process, after an initial Alert level is reached, the flow rate is changed. If the detector sensing the signal output level of the EC cell senses a decrease in signal level, with predetermined ranges of magnitude and duration which may be dependent on the particular gas/sensor combination in use, it is taken as a verification that the detecting and measuring circuitry is operating correctly, that the first measurement is not background from the sensor, and that a concentration of the gas above the preset Alert level has been confirmed. An Alarm is then generated.

An alternative quick-reaction verification process also changes the gas flow rate after a predetermined concentration of gas C1 at the Alert level has been detected at the initial flow rate. The system then changes the flow rate to F2 and measures the rate of change and the polarity of the output signal of the EC cell over a short time. The rate of change must meet predetermined duration and magnitude values, depending on the type of gas being monitored, the type of EC cell being used, and the two flow rates at which the output signal of the sensor is measured or sampled by the system. If the rate of change and the polarity of the output signal of the EC cell is, for example, negative (in the case of a reduction in gas flow rate), it is a reliable confirmation that the measuring system and EC cell are operational, that the signal is flow-responsive and not cell background noise, and that the Alert level of concentration has in fact been exceeded. An alarm is then generated.

The present invention also contemplates that the flow rate of the gas being monitored may be changed on a periodic basis (i.e. cycled repetitively between F1 and F2), permitting the verification process to be further expedited by reducing the total lapsed time for the first and second sensor measurements. Periodic cycling of the flow rates may also improve the accuracy of the sensor readings at the two flow rates. For example, a baseline can be established for the "Alert" level at the first flow rate F1 which may improve accuracy and reduce the time for verification.

The quick-reaction verification processes of the present invention are advantageous because conventional measuring systems typically record detected signal levels and such systems are under control of a data processor so that computation of signal levels, polarities and change rates is rapid, straightforward and requires no additional hardware.

Of significance, however, are the following factors: (1) fault verifications incorporating a quick-reaction technique will reduce the total time for an Initial Warning measurement and confirmation to a matter of a few seconds, as compared with the ninety seconds or more which would typically be required for two successive EC cell signal measurements, changing of flow rates and corresponding computations of gas concentration levels; and (2) the second reading at a different flow rate confirms that the EC cell is measuring a gas response, not sensor background signal.

Other features and advantages of the present invention will be apparent to persons skilled in the art from the following detailed description of various embodiments, accompanied by the attached drawing wherein identical reference numerals will be used to refer to the various steps taken in the present invention.

DETAILED DESCRIPTION OF THE ILLUSTRATED EMBODIMENT

Figure 1:
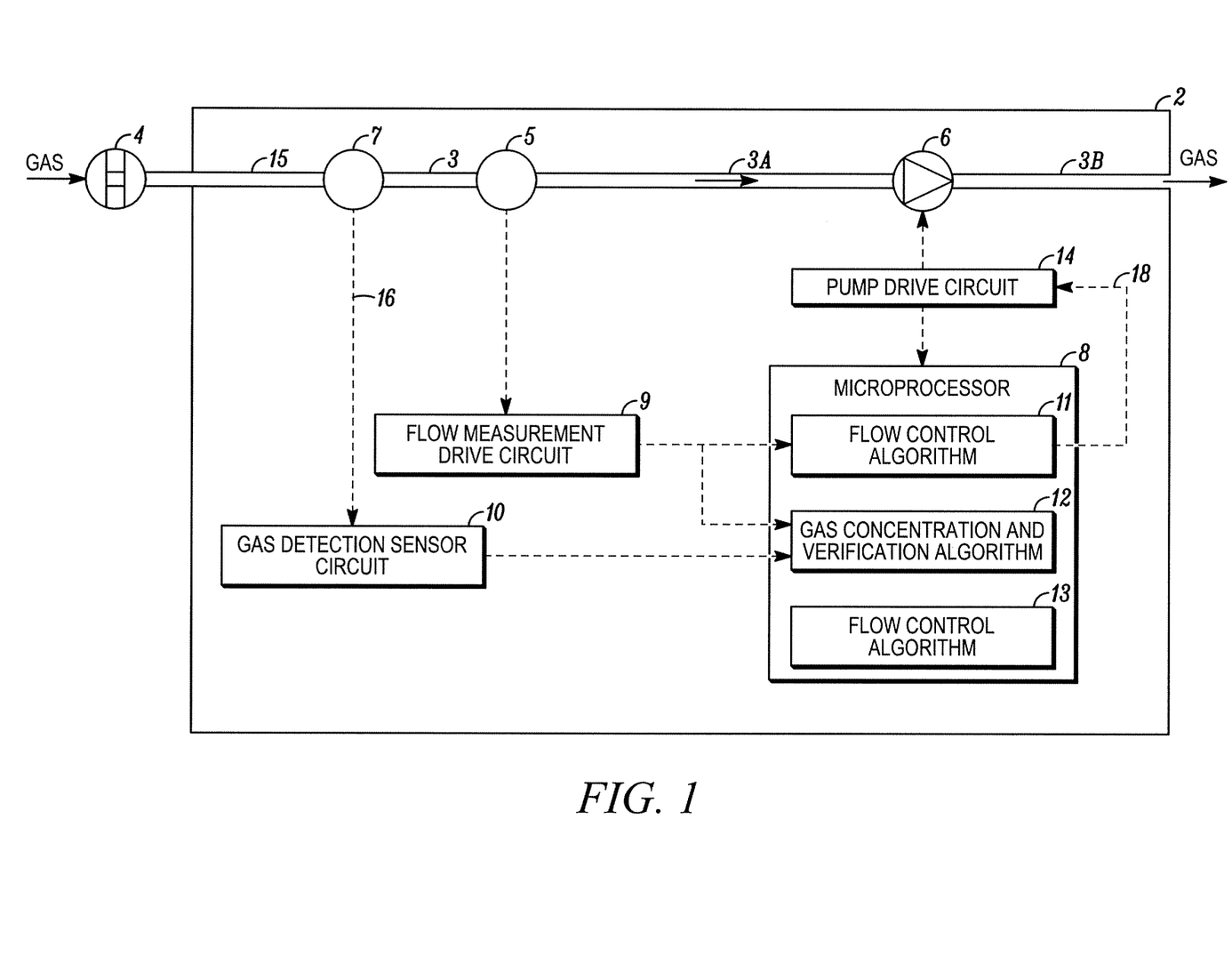
FIG. 1 is a schematic diagram of a gas detection and monitoring system incorporating the present invention.

Referring first to FIG. 1, gas is drawn from a volume being monitored through a filter 4 to a gas detection or monitoring instrument 2, which may be referred to as an aspirator. The gas being monitored is fed from the filter 4 through an inlet passage 15 to an electrochemical cell 7 ("sensor"). The gas is then routed through a passage 3 to a flow measuring device (flow meter) 5. The gas is then routed through a passage 3A to a gas pump 6 which returns the gas to the system being monitored through an outlet passage 3B. Pump 6 may preferably be a conventional diaphragm pump, having a controllable flow rate as described further below.

The EC cell 7 generates an electrical signal which is coupled along lead 16 to a conventional gas detection sensor circuit 10 which detects the signal of the EC cell 7 and processes it to a digital electrical signal representative of the output of the EC cell 7. This digital signal, in turn, is fed to a processor-based controller 8 which is programmed according to a gas concentration measurement and verification algorithm 12, below described in connection with FIG. 4. Typically, the gas being detected by the sensor is a very small part of the gas volume being monitored, but it could be a detrimental or toxic gas.

The flow meter 5 may generate an analog signal transferred to a flow measurement drive circuit 9 which generates a digital signal representative of the flow rate of the gas passing through passage 3. The output signal of the flow measurement drive circuit is fed to the controller 8, which comprises a data processor (which may be a microprocessor) programmed according to a flow control algorithm 11 and a gas concentration measurement and verification algorithm 12. The output of the processor 8 from the flow control algorithm 11 is fed to a pump drive circuit 14 which, in turn, controls the pump 6 to effect a predetermined flow rate for the gas being monitored.

The flow meter 5, flow measurement drive circuit 9, data processor 8, pump drive circuit 14 and pump 6 form a closed loop feedback control circuit to cause the flow of the gas being monitored to a predetermined rate determined by an operator and controlled by the processor 8. A first desired flow rate F1 is stored in the data processor 8 and optimized for the particular EC cell being used. Specifically, the first predetermined flow rate is preferably set to the flow rate at which the particular EC cell 7 being used, operates at maximum accuracy, which may vary depending upon the EC cell itself and the gas being detected. This information is available to users from the manufacturer of the EC cell. By way of example only, and without intending to limit the invention, if the gas sought to be monitored is hydrogen sulfide, an EC cell Part. No. MIDAS-S-H2S available from Zellweger Analytics, Inc. of Lincolnshire, Ill. U.S.A. may be used. All necessary operational data is known and publicly available.

Figure 5:
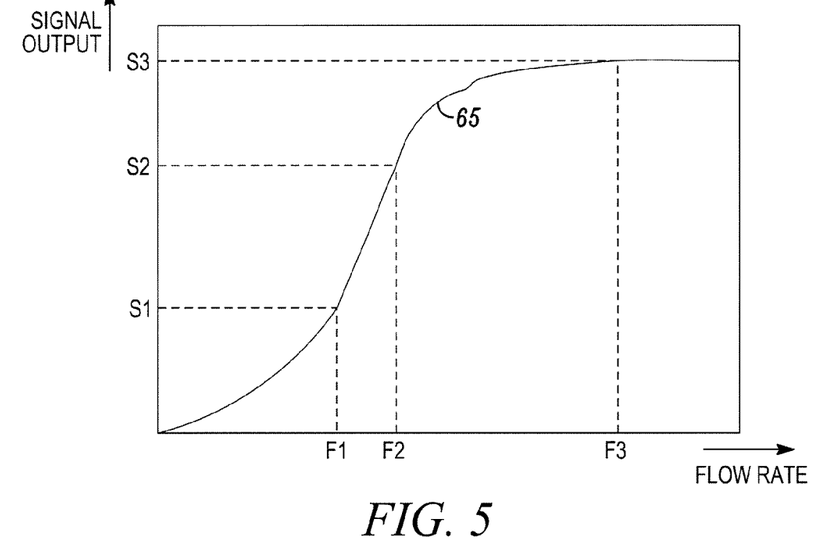
FIG. 5 is a graph showing the relationship between flow rate and signal output for an idealized EC cell.

Turning now to FIG. 5, there is illustrated an idealized graph showing the general relationship, for an EC cell, between flow rate and the gas-responsive (i.e. excluding cell background) signal output. The relationship is identified in the drawing by reference numeral 65, and it is seen to be a non-linear, but a monotonically increasing function. That is, as the flow rate increases, the output signal of the cell also increases, but the relationship is not linear for all values of flow rate, and in fact the signal begins to approach an upper limit as illustrated. Such relationships between a toxic gas being monitored and the appropriate EC cell are known in the industry, and are referred to herein as "diffusion limited" response characteristics, referring to the diffusion layer associated with typical electrochemical cells. There are a number of toxic gases which can be detected by separate EC cells, although some EC cells have the capacity to monitor more than one gas.

It will also be appreciated from FIG. 5 that for the exemplary relationship shown, which is generally representative of many EC cells of interest, if flow rate F2 is the desired or "optimized" flow rate for operating the system at a quiescent level of concentration of the gas, and the flow rate is reduced from F2 to F1, the change in gas responsive signal, from S2 to S1, for the same gas concentration is substantial, and readily detectable, although verification can be obtained by increasing the flow rate since a differential change in the output signal is also experienced for flow rate increases in diffusion-limited response characteristics, as illustrated in FIG. 5.

Figure 2:
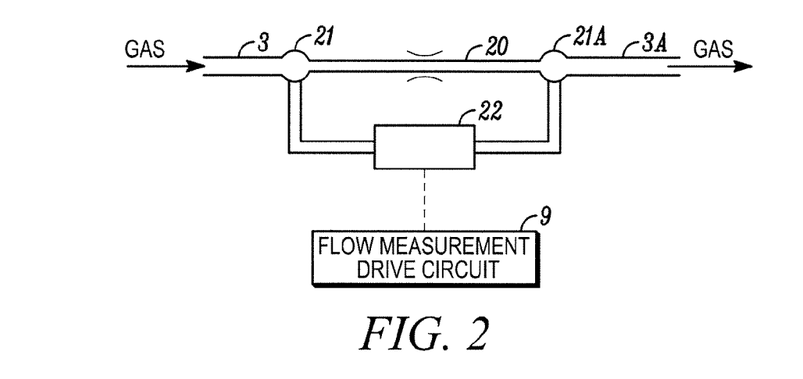
FIG. 2 is a diagrammatic view of the flow measuring device of FIG. 1.

Referring now to FIG. 2, the flow meter 5 is seen in more detail as including a flow restrictor 20 forming a laminar flow of the gas being monitored. The gas flows from the passage 3 through a first tee fitting 21 to the restrictor 20, and then through a second tee 21A to the passage 3. A pressure transducer 22 is coupled to the tees 21, 21A respectively for sensing the pressure difference across the restrictor 20. Because the flow is laminar through the restrictor 20, the differential pressure sensed by the transducer 22 is representative of flow. The output of the transducer 22 is fed to a flow measurement drive circuit 9 for converting the electrical signal to an appropriate level and digital format which is then fed to the data processor 8.

Figure 3:
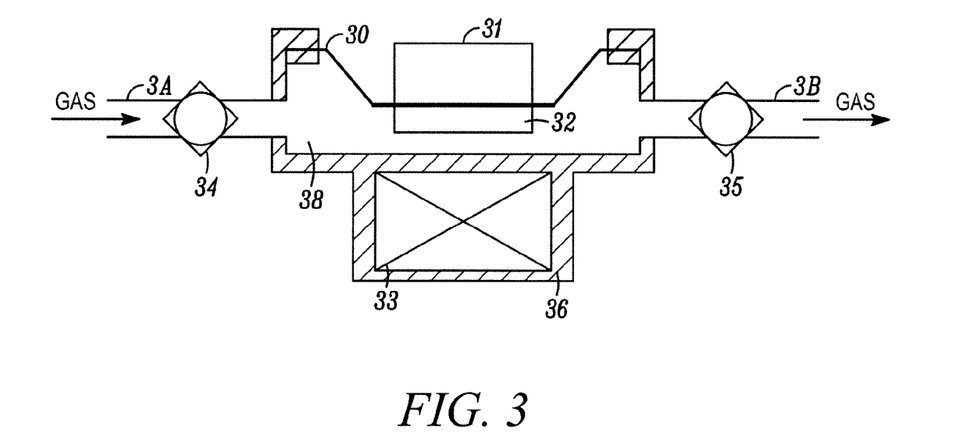
FIG. 3 is a diagrammatic showing of the gas pump of FIG. 1.

The diaphragm pump 6 is seen in FIG. 3 as including a permanent magnet 32 mounted to a diaphragm 30, to which a counterweight 31 is also fixed. The diaphragm 30 has its periphery secured to a frame or housing 36 which also houses an electromagnet 33 driven by the flow control algorithm 11 of the data processor 8 along lead 18 (FIG. 2). Flow control algorithm 11 generates an output signal along line 18 to the pump drive circuit 14 which controls the pump 6 to operate at a predetermined but controlled flow rate.

Check valves 34 and 35 (FIG. 3) are coupled in series with passages 3A and 3B of the monitor respectively to insure unidirectional flow of the gas pumped by the action of the pump 6 in the direction of the arrows in FIG. 3. As is known, the magnetic field of the electromagnet 33 alternately forces the diaphragm to move periodically away from and toward the electromagnet 33, thereby alternately expanding and contracting the volume of chamber 38 defined by the diaphragm 30 and the housing 36. As the chamber 38 expands, gas flows into the chamber 38 through check valve 34. As the chamber 38 contracts under the magnetic force of attraction, gas is forced through the outlet check valve 35 into passage 3B. As will be recalled, the data processor 8 is provided with a table of identifications of specific EC cells and their associated gas flow rate for maximum accuracy.

Figure 4:
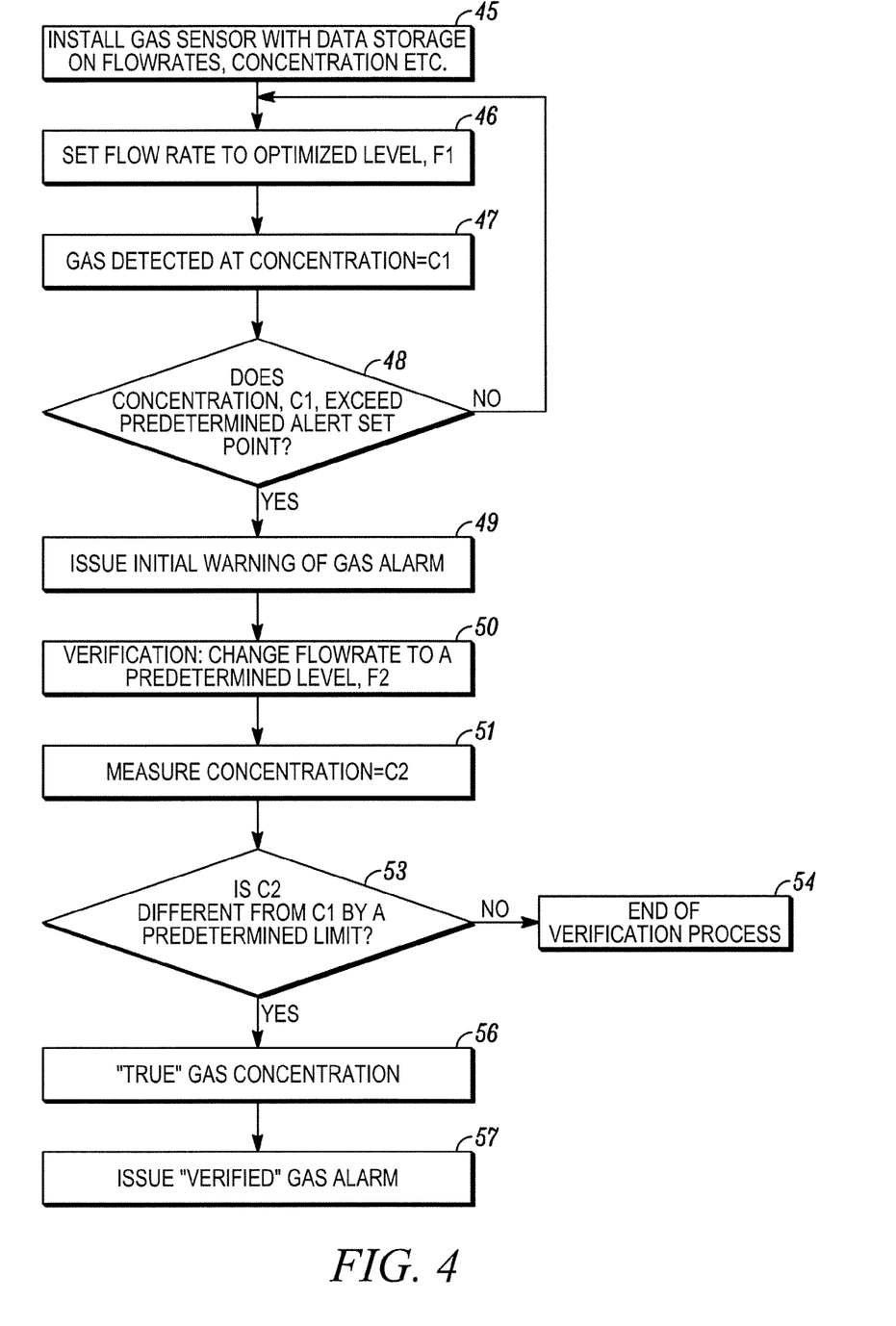
FIG. 4 is a flow chart of the program for the gas detection and measurement algorithm for a first embodiment of the invention.

Turning now to FIG. 4, there is shown a flow chart of the gas concentration measurement and verification algorithm 12 of FIG. 1. In block 45, the operator installs a gas sensor cell having tabulated look-up data stored in the data processor 8 on the flow rate, accuracy and concentration for that particular sensor or EC cell and the particular gas under surveillance, an example of which is given above. In block 46, the program sets the flow rate to the detection level, F1, for best accuracy for the EC cell and gas of interest, as determined by the operator or stored data. In block 47, the gas is detected and a value is calculated representing the concentration, C1, of the gas detected by the sensor at a first flow rate, F1. The data processor 8 continuously periodically monitors concentration C1 and, in block 48, determines whether the concentration C1 exceeds a predetermined safe set point which may be referred to as the Alert level because it has not been verified. The Alert level and the Alarm level of concentration are the same. If the program determines that the predetermined Alert level is not achieved, the program loops back to block 46 for continued measurement and monitoring. Typically, it takes about ninety seconds or more to make a complete determination of concentration from the sensed signals and the known, controlled flow rate, F1.

If, in block 48, it is determined that the concentration C1 does equal or exceed the Alert level, the program issues an Initial Warning to the operator, and changes the flow rate to a second predetermined level, F2, in Block 49.

The Initial Warning may take many forms, such as audible or visual signals, or recorded or displayed textual material, or combinations thereof. However, no remedial action is taken at this time by the monitoring system.

Thereafter, the program enters into a verification procedure, beginning with block 50 in FIG. 4.

In block 50, after the data processor 8 has changed the flow rate of the gas to a second predetermined level, F2, the value of which is stored in the data associated with that particular EC cell, the system again measures the concentration (C2) of the gas being detected, as indicated in block 51. Measurement C2 thus represents the concentration of the gas being detected at the second predetermined flow level, F2. The second flow rate F2 preferably may be a lower flow rate than F1, typically less than half the first preset flow rate F1. However, persons skilled in the art will appreciate that other flow rates, including greater flow rates may be used for the second flow rate setting.

In decision block 53 the system determines whether the concentration C2 differs from the concentration measurement C1 by a predetermined amount. This amount depends on factors, including the response characteristic of the sensor. A reading indicating that there is no substantial difference between concentrations C1 and C2 is taken as an indication that an error in the measuring system has occurred, such as might be caused by component failure, sensor background signal, subsystem error, RFI or other transient effect. The program, as indicated in block 54, then determines that the first measurement, C1, at the first or optimum flow level, F1, for present purposes, cannot be verified, and a corresponding message is transmitted to the operator, and may be displayed and/or recorded. Block 54 represents the end of the attempt by the system to provide further verification of the gas concentration, and the system notifies the operator and returns to the main loop at block 51 to continue measuring concentration levels.

If, in block 53 it is determined that the second gas concentration measurement C2 at flow level F2 has changed and is different from the original measurement of concentration C1 by at least a predetermined amount (which is also dependent on other factors) and has changed in the proper direction (if F2 is less than F1, then C2 must be less than C1, not greater), the program determines in block 56 that the first measurement C1 was an accurate or TRUE gas concentration measurement, and the system issues a corresponding ALARM, and may include a notice of verified gas concentration measurement in block 57.

Figure 6:
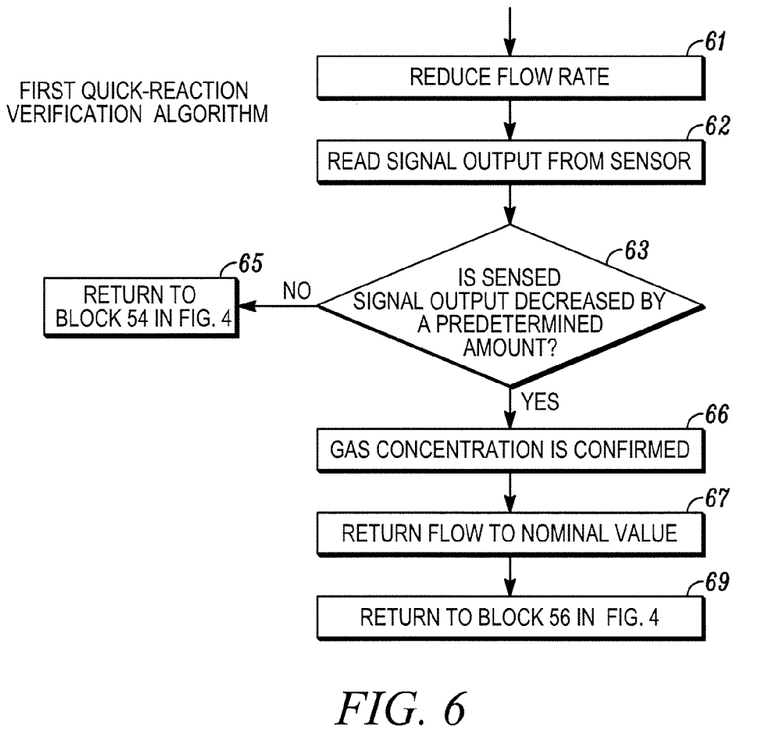
FIG. 6 is a flow chart showing the operation of the system for a second embodiment, which includes a first quick-reaction confirmation sequence.

In FIG. 6, there is shown an algorithm for a first quick-reaction verification process which would provide a verified ALARM condition (and/or take remedial action) in a shorter time than the procedure of FIG. 4. This algorithm replaces blocks 49-56 in the algorithm of FIG. 4. Turning then to FIG. 6, once it is determined in block 48 of FIG. 4 that a sensor measurement of the EC cell has detected a gas concentration C1 in excess of a predetermined Alert set point, an Initial Warning is signaled, and the flow rate is reduced to a predetermined flow rate F2. As indicated above, it is preferred to reduce the flow rate, but the process will work if the flow rate is increased in block 61.

While the flow rate is being changed in block 61, the EC cell continues to read or sample the output signal from the sensor cell, as indicated in block 62. In block 63, the data processor 8 determines whether the sensed signal output of the EC cell at F2, as determined in block 62, decreases by a predetermined amount after the flow rate has been reduced. If the output signal of the EC cell does not change, as determined in block 63, after the flow rate has been changed to F2 in block 61, the system determines that the first reading C1 at initial Alert set point determined in block 48 was caused by error, which could include sensor background signal, an equipment malfunction, or an exterior source such as RFI. In this case, the algorithm proceeds along the "NO" path 64 in FIG. 6 and ends the first quick-reaction verification algorithm of FIG. 6 to block 54 in FIG. 4, as diagrammatically represented by the block 65 in FIG. 6.

If, on the other hand, in block 63 the system determines that the sensed signal output has decreased by a predetermined level in block 63, the system takes this indication as a confirmation or verification that the Alert signal which indicated the concentration C1 had exceeded the first predetermined Alert set point is, in fact, correct, and the Alert level gas concentration is confirmed in block 66 and an Alarm generated; and the operator is notified or remedial action taken automatically or both. The system thereafter changes the flow rate back to F1 in block 67, and again exits the quick-reaction verification algorithm, but returns to block 56 in FIG. 4, as indicated by the block 67 in FIG. 6.

The primary advantage of the quick reaction verification algorithm of FIG. 6, as compared to the verification algorithm of FIG. 4 is that the verification process of FIG. 6 can be completed within a few seconds of the original determination that gas concentration exceeds a predetermined Alert set point in block 48, whereas the determination of concentration C2 at the second flow rate F2 in blocks 50, 51 of the verification algorithm of FIG. 4, could take as long as ninety seconds or thereabouts to complete.

Figure 7:
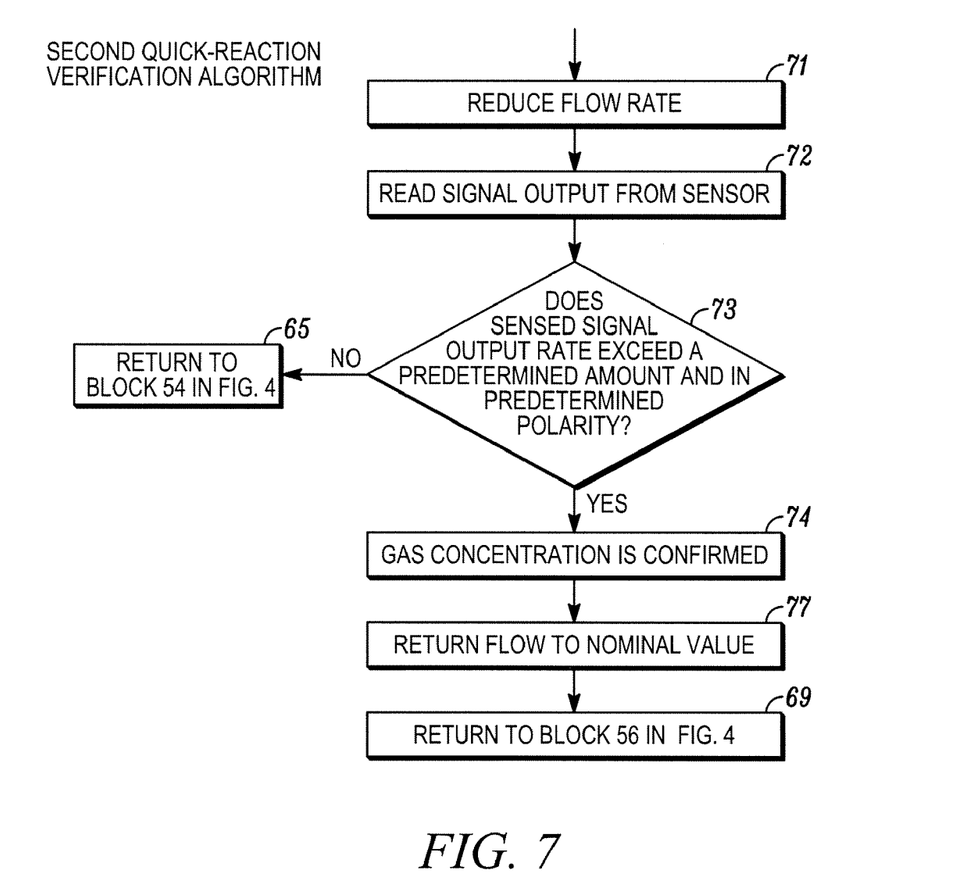
FIG. 7 is a flow chart of the program for the gas detection system of FIG. 1 for a second quick-reaction verification sequence embodied in the system of FIG. 1.

Turning now to a second quick reaction verification algorithm as seen in FIG. 7, as with the algorithm of FIG. 6, once the system determines that the predetermined safe concentration C1, representative of a predetermined Alert set point, is exceeded, an Initial Warning may be signaled to alert the operator, and the flow rate of the gas is reduced from F1 to F2 in block 71, while the signal output of the sensor is continued to be read by the data processor 8, as represented in block 72.

It will be recalled that not only is the signal output stored, but the rate of change of the sensor signal is computed and stored by the data processor 8. In block 73, the data processor 8 determines whether the rate of change of the output signal of the EC cell exceeds a predetermined amount and the polarity of the change. That is, the data processor 8 differentiates the sensor output signal and determines the polarity of the change. If, for example, the flow rate is reduced from F1 to F2 in block 71 and the polarity of the derivative of the output signal of the sensor is negative (since the sensor output signal should be reduced when the flow rate is reduced) and exceeds a predetermined amount as determined in block 73, at the new operating point, it is taken as a determination that the measuring elements of the system are operative and that the concentration level measured in block 48 is confirmed in block 74 of FIG. 9. The system signals a confirmed Alarm, then returns the flow rate to its nominal or original value in block 77, and the system returns to block 56 in FIG. 4. If, on the other hand in block 73, after the flow rate is reduced to F2, the derivative of the sensor output signal does not both exceed a predetermined amount and have the required polarity as determined in block 73, then the system so notifies the operator without signaling an Alarm, and returns to block 54 in FIG. 4.

The quick reaction verification algorithm of FIG. 9 will reach a determination of a confirmed Alarm condition in substantially less time then that of FIG. 4 because determining the rate of change of the sensor signal and the polarity of the signal change in block 73 by the data processor 8 can be done in a very short period of one second or less, and it can then be compared with a predetermined level of rate of change even more quickly. Again, the verification algorithm of FIG. 9 takes a substantially less time than that of FIG. 4 because it does not require that the verification algorithm determine the concentration of the gas being monitored at flow level F2.

The nature of the visual or audible signals, displays or recordings for the Initial Warning and Verified Alarm conditions preferably are different so that the operator may differentiate them and immediately determine the status of the monitoring system.

To further reduce the verification time in any of the three methods presented above as well as to increase accuracy, it may be desired to continuously cycle the flow rate between F1 and F2. Once a measurement from the sensor 7 is taken, the concentration must then be determined by the data processor 8 according to known procedures, and this determination takes time.

In an alternative embodiment, the data processor 8 changes the flow rate to F2 as soon as the sampled signal from the sensor is received by the data processor and while the computation and determination of C1 is being made. The confirmation of block 66 of FIG. 6 will thus be sooner in time because the sensor measurement at F2 may be completed or near completion by the time concentration C1 is determined.

Moreover, by periodically cycling the flow rate of the gas, the data processor can make measurements of the average or quiescent values of sensor signal output at F1 and F2, determine and employ averaging and other statistical techniques to determine and compensate for noise and background signal, determine a baseline signal for concentration levels and flow rates, and provide other information.

The two phases of the periodic cycling need not be of the same time duration depending on the verification technique used. Further, if one of the quick-response verification techniques described above is employed and the flow rate is cycled, the duration of the signal forcing pump 6 to operate at flow rate F2 may be considerably shorter than operation at flow rate F1, and a verification determination may be made almost immediately after the computation of C1 is complete, thus shortening the overall time required to complete a measurement and verification cycle.

Having thus disclosed in detail a number of embodiments of the present invention, persons skilled in the art will be able to modify certain of the steps which have been disclosed, and to substitute equivalent components or structure for that which has been described; and it is, therefore, intended that all such modifications and substitutions be covered as they are embraced within the spirit and scope of the appended claims.

We claim:

1. Apparatus for detecting and confirming that a concentration of a selected gas in a gaseous mixture is at least as great as a predetermined level of concentration, comprising:
  a conduit for coupling to a gaseous mixture;
  a sensor for detecting gas in the conduit and generating a signal representative of a concentration of a selected gas present in the mixture;
  a pump having a controllable flow rate, the pump pumping the gaseous mixture through the conduit at a first flow rate;
  control circuits coupled to the sensor and the pump, the control circuits determine a first concentration of the selected gas at the first flow rate, and responsive at least in part thereto, causing the pump to pump the mixture at a second, different flow rate, the control circuits determine a second concentration of the selected gas at the second flow rate, the control circuits use the concentration at the first flow rate and the concentration at the second flow rate in establishing the presence of a selected gas condition.

2. The apparatus of claim 1 where the control circuits compare the concentrations to confirm or deny validity of the determined first concentration.

3. The apparatus of claim 2 where the control circuits periodically cycle the flow rate between the two flow rates.

4. The apparatus of claim 1 where the control circuits receive the signal from the sensor after the flow rate is changed to the second rate and determine the amount of any corresponding change in the magnitude thereof to confirm or deny the accuracy of the determined first concentration.

5. The apparatus of claim 4 where the control circuits operate the pump such that the second flow rate is lower than said first flow rate.

6. The apparatus of claim 1 where the control circuits continue to receive the output signal from the sensor after the change in flow rate and determine concentration change to confirm the validity of the first determined concentration at the first flow rate.

7. The apparatus of claim 6 wherein the sensor comprises an electrochemical cell.

8. The apparatus of claim 7 where the control circuits operate the pump to periodically cycle the flow rates between the first and second flow rates.

9. The apparatus of claim 7 where the control circuits compare the concentrations to one another to confirm or deny validity of the determined first concentration.

10. The apparatus of claim 1 where the control circuits operate the pump such that the second flow rate is lower than the first flow rate to determine that the sensor's signal decreases when the flow rate is decreased.

* * * * *